(12) United States Patent
Does et al.

(10) Patent No.: US 12,082,916 B2
(45) Date of Patent: Sep. 10, 2024

(54) BIORESORBABLE RF COILS FOR POST-SURGICAL MONITORING BY MRI

(71) Applicants: Vanderbilt University, Nashville, TN (US); Northwestern University, Evanston, IL (US)

(72) Inventors: Mark D. Does, Nashville, TN (US); John A. Rogers, Wilmette, IL (US)

(73) Assignees: Vanderbilt University, Nashville, TN (US); Northwestern University, Evanston, IL (US)

( * ) Notice: Subject to any disclaimer, the term of this patent is extended or adjusted under 35 U.S.C. 154(b) by 37 days.

(21) Appl. No.: 17/798,193

(22) PCT Filed: Mar. 1, 2021

(86) PCT No.: PCT/US2021/020307
§ 371 (c)(1),
(2) Date: Aug. 8, 2022

(87) PCT Pub. No.: WO2021/178315
PCT Pub. Date: Sep. 10, 2021

(65) Prior Publication Data
US 2023/0103510 A1 Apr. 6, 2023

Related U.S. Application Data

(60) Provisional application No. 63/082,332, filed on Sep. 23, 2020, provisional application No. 62/984,155, filed on Mar. 2, 2020.

(51) Int. Cl.
*A61B 5/05* (2021.01)
*A61B 5/055* (2006.01)

(52) U.S. Cl.
CPC ............. *A61B 5/05* (2013.01); *A61B 5/055* (2013.01); *A61B 2505/05* (2013.01)

(58) Field of Classification Search
CPC ....... A61B 5/05; A61B 5/055; A61B 2505/05; A61B 5/0507; A61B 5/4029;
(Continued)

(56) References Cited

U.S. PATENT DOCUMENTS 5,055,288 A 10/1991 Lewis et al.
8,666,471 B2 * 3/2014 Rogers ................. A61B 5/6867
607/116

(Continued)

FOREIGN PATENT DOCUMENTS

JP 2003-61929 A 3/2003

OTHER PUBLICATIONS

Choi et al., Biodegradable Polyanhydrides as Encapsulation Layers for Transient Electronics. Adv. Funct. Mater. 2020, 30, 2000941. https://doi.org/10.1002/adfm.202000941.
(Continued)

*Primary Examiner* — G. M. A Hyder
(74) *Attorney, Agent, or Firm* — Blank Rome LLP

(57) ABSTRACT

An implantable bioresorbable radio frequency (RF) coil for high-resolution and high-specificity post-surgical evaluating or monitoring with magnetic resonance imaging (MRI) is disclosed. The coil includes a bioresorbable conductor configured to be resorbed within a patient while the coil is implanted in the patient. In one embodiment, the target application of this coil is the evaluation or monitoring (via MRI) of peripheral nerve regeneration following surgical repair.

19 Claims, 6 Drawing Sheets

(58) Field of Classification Search
CPC .......... G01R 33/3642; G01R 33/34084; H01B 1/08; H01F 5/00
See application file for complete search history.

(56) References Cited

U.S. PATENT DOCUMENTS

| | | |
|---|---|---|
| 2010/0152811 A1 | 6/2010 | Flaherty |
| 2011/0046707 A1 | 2/2011 | Lloyd et al. |
| 2013/0140649 A1 | 6/2013 | Rogers et al. |
| 2014/0200626 A1* | 7/2014 | Campbell .......... A61N 1/37516 607/46 |
| 2014/0323968 A1* | 10/2014 | Rogers ................ H05K 1/0275 29/829 |
| 2017/0020402 A1* | 1/2017 | Rogers ................ A61B 5/0031 |
| 2020/0188657 A1* | 6/2020 | Ray ...................... A61N 1/375 |

OTHER PUBLICATIONS

Bilgen, M., (2006) Inductively-overcoupled coil design for high resolution magnetic resonance imaging BioMedical Engineering OnLine 5(1), 3. https://dx.doi.org/10.1186/1475-025x-5-3).

Edelstein, W., et al., Resonance, O., 1986 (1986), Electronic decoupling of surface-coil receivers for NMR imaging and spectroscopy Elsevier 67(1), 156 161. https://dx.doi.org/10.1016/0022-2364(86)90421-x.

International Search Report and Written Opinion from PCT/US2021/020307 dated May 25, 2021.

\* cited by examiner

BIORESORBABLE RF COILS FOR POST-SURGICAL MONITORING BY MRI

CROSS REFERENCE TO RELATED APPLICATION(S)

This application is a national stage of International Application No. PCT/US2021/020307 filed Mar. 1, 2021, which claims priority to U.S. Provisional Patent Application Ser. No. 63/082,332, filed on Sep. 23, 2020 and U.S. Provisional Patent Application Ser. No. 62/984,155, filed on Mar. 2, 2020, both of which are hereby incorporated herein by reference in their entireties.

GOVERNMENT SPONSORSHIP

This invention was made with government support under Grant No. NIBIB 1R21EB027881 awarded by NIH. The government has certain rights in the invention.

FIELD OF THE INVENTION

Embodiments are in the field of systems and methods for imaging. More particularly, embodiments disclosed herein relate to systems and methods for imaging, including a bioresorbable radio frequency (RF) coil, which enable applications such as quantitative monitoring/evaluations of nerve regeneration following surgical repair.

BACKGROUND OF THE INVENTION

Magnetic resonance imaging (MRI) is a versatile imaging modality with contrast that is sensitive to a myriad of physical, chemical, and functional characteristics of tissue. Harnessing these sensitivities to provide quantitative and specific imaging biomarkers is a central idea of many MRI research programs. Often, the critical barrier to progress in MRI method development, particularly quantitative MRI (qMRI) method development, is the signal-to-noise ratio (SNR) achievable for methods that provide sufficiently high resolution in a clinically practical scan time.

One approach to mitigate this barrier, at least for narrowly targeted studies, is through the use of small RF coils, which can provide high SNR over a small volume of tissue. Surface coils have long been used for this purpose, particularly for magnetic resonance spectroscopy (MRS) studies, as have endoscopic coils to reach tissues such as the prostate gland. To reach arbitrary locations in animal studies, RF coils have been surgically implanted and wirelessly connected via inductive coupling. In its first application, the wireless implanted MRI probe was named "WIMP". Experimental studies have reported that a WIMP provides SNR increases of 2-12×, and theoretical calculations indicate that even greater gains are possible for deeper coils. One can imagine human clinical applications for the WIMP, particular if the coil could be implanted at the time of an otherwise necessary surgery. However, the benefit of higher SNR is unlikely to outweigh the risk of surgically removing the WIMP or leaving it in place permanently, and so, for at least those reasons, the conventional WIMP has little or no future as a clinical tool.

Thus, it is desirable to provide an MRI imaging system, including a bioresorbable RF coil, that is able to overcome the above disadvantages and which enables applications such as quantitative monitoring/evaluations of nerve regeneration following surgical repair, which are achieved via high SNR and high image resolution MRI over a targeted volume of tissue.

Advantages of the present invention will become more fully apparent from the detailed description of the invention hereinbelow.

SUMMARY OF THE INVENTION

Embodiments are directed to a bioresorbable RF coil configured to be implanted in a patient. The coil includes a bioresorbable conductor configured to be resorbed within the patient while the coil is implanted in the patient.

Embodiments are also directed to an imaging system. The imaging system includes a bioresorbable RF coil configured to be implanted in a patient. The coil includes a bioresorbable conductor configured to be resorbed within the patient while the coil is implanted in the patient. The imaging system also includes an MRI device configured to image the patient using the coil while the coil is implanted in the patient.

Embodiments are further directed to a method for evaluating or monitoring a patient by MRI. The method includes implanting a bioresorbable RF coil in a patient. The coil includes a bioresorbable conductor configured to be resorbed within the patient while the coil is implanted in the patient. The method also includes imaging the patient with the MRI using the coil while the coil is implanted in the patient.

Additional embodiments and additional features of embodiments for the bioresorbable RF coil, imaging system, and method for evaluating or monitoring a patient by MRI are described below and are hereby incorporated into this section.

BRIEF DESCRIPTION OF THE DRAWINGS

The foregoing summary, as well as the following detailed description, will be better understood when read in conjunction with the appended drawings. For the purpose of illustration only, there is shown in the drawings certain embodiments. It is understood, however, that the inventive concepts disclosed herein are not limited to the precise arrangements and instrumentalities shown in the figures. The detailed description will refer to the following drawings in which like numerals, where present, refer to like items.

DETAILED DESCRIPTION OF THE INVENTION

Figure 1A:
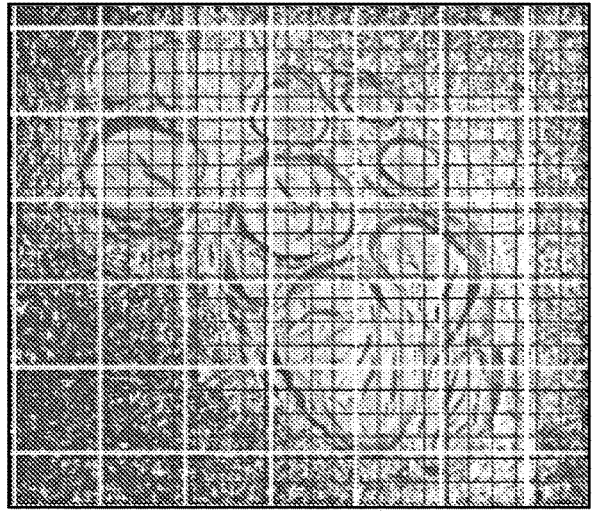
FIG. 1A is a drawing illustrating a histological section of a human median nerve.

It is to be understood that the figures and descriptions of the present invention may have been simplified to illustrate elements that are relevant for a clear understanding of the present invention, while eliminating, for purposes of clarity, other elements found in a typical MRI device or typical method of using MRI. Those of ordinary skill in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different than those shown in the drawings. Reference will now be made to the drawings wherein like structures are provided with like reference designations.

Before explaining at least one embodiment in detail, it should be understood that the inventive concepts set forth herein are not limited in their application to the construction details or component arrangements set forth in the following description or illustrated in the drawings. It should also be understood that the phraseology and terminology employed herein are merely for descriptive purposes and should not be considered limiting.

It should further be understood that any one of the described features may be used separately or in combination with other features. Other invented devices, systems, methods, features, and advantages will be or become apparent to one with skill in the art upon examining the drawings and the detailed description herein. It is intended that all such additional devices, systems, methods, features, and advantages be protected by the accompanying claims.

Research Strategy
Significance

Recent advances in materials engineering have resulted in the development of bioresorbable electronic devices, including intracranial temperature and pressure sensors, heating devices for post-surgical infection control, and electrophysiological recording systems that can map neurological activity on the cortical surface of the brain. These devices can be surgically implanted and function for some period of time (days to weeks, or longer) before being harmlessly absorbed by the body. In this disclosure, the inventors harness those advances to develop bioresorbable RF coils for post-surgical tissue monitoring/evaluation with high-SNR, high-resolution MRI.

To differentiate this device from the conventional WIMP, this disclosure refers to its bioresorbable inductively-coupled coil as "BIC". BIC technology may be employed in many surgical procedures, but the disclosure hereinbelow describes the evaluation of peripheral nerves following surgical repair because it is an important clinical problem.

Peripheral Nerve Injury/Repair/Regeneration

Peripheral nerve damage is a common consequence of trauma (>100,000 cases in the US and Europe annually), and in many cases surgery is needed to repair the nerve. Unfortunately, outcomes are highly variable and large fractions of patients (~50%) experience only moderate (or less) motor and sensory recovery. A common clinical problem associated with nerve repair surgery is knowing whether or not the repair will be effective in restoring function. Nerve regeneration is slow (~1 mm/d), and so it may be months after surgery before the regenerating axons innervate the target tissue. During this delay, muscle fibers rapidly atrophy (~70% reduction in cross-sectional area in 2 months) and the capacity of axons to regenerate is reduced. Overall, clinical outcomes are worse due to delay of nerve repair, and by the time a failed repair is identified (e.g., through lack of functional response), revisional surgery may not be a viable option.

Current neurodiagnostics, such as electromyography and nerve conduction studies, are of limited utility in severely damaged nerves, providing an incomplete picture of nerve microstructural features until target reinnervation occurs. High-resolution ultrasound has shown the ability to accurately identify transected nerves; however, traumatic injuries have proven difficult for diagnosis using ultrasonography due to the presences of large hematomas, extensive skin lacerations, edema, and disruption of the normal anatomy. Furthermore, no studies have shown the ability of high-resolution ultrasonography to detect early nerve regeneration, which ultimately would indicate whether or not an additional surgical intervention is required. Thus, physicians are limited to a 'wait and watch' approach based on qualitative measures obtained from patient history and/or physical exam. This leads to a suboptimal management of peripheral nerve injuries, which in turn can lead to increased instances of irreversible muscle atrophy, paralysis, and/or formation of painful traumatic neuromas. MRI, with its excellent soft-tissue contrast, is a promising modality to solve these problems, but has its own challenges.

MRI of Nerve Injury

MR neurography (MRN) began more than 25 years ago and now includes an assortment of different MRI methods for visualizing peripheral nerves. Nerves can be visualized at high resolution (≈0.3 mm in-plane) with $T_2$-contrast and/or fat-suppression. Following structural damage and surgical repair, a nerve exhibits a marked increase in $T_2$, which aids in visualization, but changes in $T_2$-contrast cannot be attributed to any specific change in the nerve microstructure. Alternatively, there are a number of qMRI methods that can provide more specific evaluation of a nerve, the most widely used of which is diffusion tensor imaging (DTI).

From the diffusion tensor, various scalar metrics can be extracted, including fractional anisotropy (FA), which reports on the degree of anisotropy of water diffusion within a voxel. As far back as 1996, in-vitro studies of diffusion found anisotropy to be higher in injured nerves with regenerating axons compared to those without, and more recent experimental studies have shown FA correlating with histological measures of healthy nerve microstructure. Similarly, other advanced qMRI methods, such as multi-compartment models of diffusion, relaxation, or magnetization transfer can provide greater microstructural specificity of a nerve. However, the resolution of each of these qMRI methods is ultimately limited by SNR, which thus limits their use to evaluate nerve injury and regeneration.

Figure 1B:
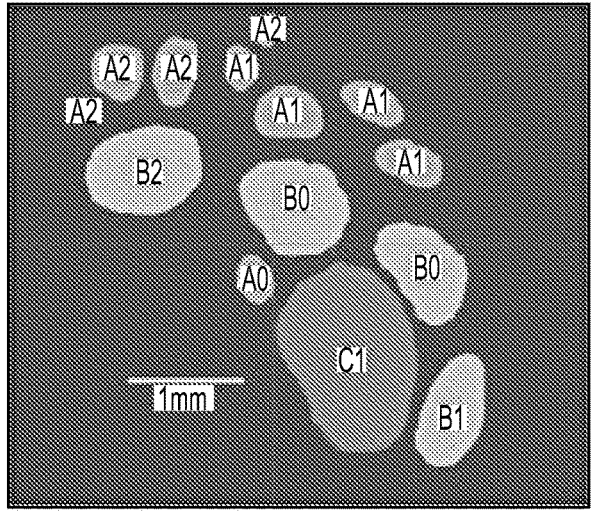
FIG. 1B is a drawing illustrating a map of segmented fascicles of the image shown in FIG. 1A.

FIG. 1A is a drawing illustrating a histological section of a human median nerve. The white grid lines show current best in-vivo DTI resolution and black grid lines show possible resolution after 14-fold SNR gain. For ease of interpretation, FIG. 1B is a drawing illustrating a map of segmented fascicles of the image shown in FIG. 1A.

Specifically, the white grid lines illustrated in FIG. 1A show a 0.75×0.75 mm² in-plane resolution, which is currently the highest resolution used for DTI evaluation of a median nerve. It is apparent from this figure that the heterogeneity resulting from fascicular structure and large connective tissue space cannot be captured at this resolution. The partial volume averaging of axon and connective tissue is particularly problematic for evaluating nerve regeneration because it reduces sensitivity of any qMRI measure to changes in the axon microstructure. Post-surgery, edema will also contribute to heterogeneity, and so a normalization (increase) in FA might report on axonal regeneration or the abatement of edema, or both. Thus, despite progress in applying DTI, MRN has not become standard-of-care for evaluating nerve regeneration, and the primary barrier to progress is SNR.

This application aims to develop and evaluate SNR gains from BICs that can be implanted distal to a repair site at the time of surgery (see FIG. 2, described more fully below) and eventually be used for applications such as MRN evaluation of surgically repaired peripheral nerve.

Innovation

This invention creates a new avenue for clinicians to acquire post-surgical diagnostic information. It is anticipated that BIC technology may be applicable to many surgical procedures, one example being the evaluation or monitoring of peripheral nerve following surgical repair. The BIC achieves a low-cost approach to provide high SNR MRI over a reduced field-of-view (FOV). These SNR gains can be used to provide higher spatial resolution and/or aid SNR-demanding qMRI, such as diffusometry, relaxometry, or MRS. Because surgery is a widely used health care tool, BICs have potential for far-reaching impact.

For the specific exemplary application targeted in this disclosure (i.e., imaging peripheral nerve following surgical repair), the BIC promises to fundamentally change clinical practice. The surgeon will be armed with more detailed evaluations of the nerve at earlier time points following surgery, enabling her/him to better decide if/when to perform a revision surgery. Ultimately, this will improve patient outcomes and reduce unnecessary procedures.

Approach

This disclosure explores a variety of exemplary BIC designs and evaluates their potential to improve the SNR, and resolution of post-surgical peripheral nerve MRI. To that end, this disclosure presents an iterative approach to design, fabrication, and testing of RF coils. The research and development plan is organized in terms of two closely coupled aims: 1) design and fabricate coils, and 2) evaluate their performance by experimental surgery and MRI.

Outline

The overall research and development plan is summarized as follows: coil designing, followed by fabrication and bench top testing, and then MRI testing.

Given the wide range of nerve sizes and depths for which a BIC might be valuable, there is no one set of criteria to define a successful design. To provide context for an effective BIC, this disclosure presents one example scenario below for which a successful BIC would largely overcome the resolution challenges of MRN.

EXAMPLE SCENARIO

A current 3T in-vivo median nerve (forearm) imaging protocol includes DTI with in-plane resolution of 0.75×0.75 mm², slice thickness=4 mm, b=800 s/mm², 16 DWI directions, 12 averaged excitations, scan time≈11 min, SNR(b=0) ≈40. As noted above and presented in FIG. 1A and FIG. 1B, this resolution is insufficient to capture the structural heterogeneity of a peripheral nerve, even in a normal, healthy state. An SNR increase of ≈14× can, in principle (pulse sequence challenges aside), be used to increase the in-plane resolution to 0.2×0.2 mm², which, is depicted with the black grid lines illustrated in FIG. 1A. With this higher resolution, it will be possible to provide qMRI characteristics of many individual fascicles, and there will be little partial, volume averaging of connective tissue space.

Figure 3:
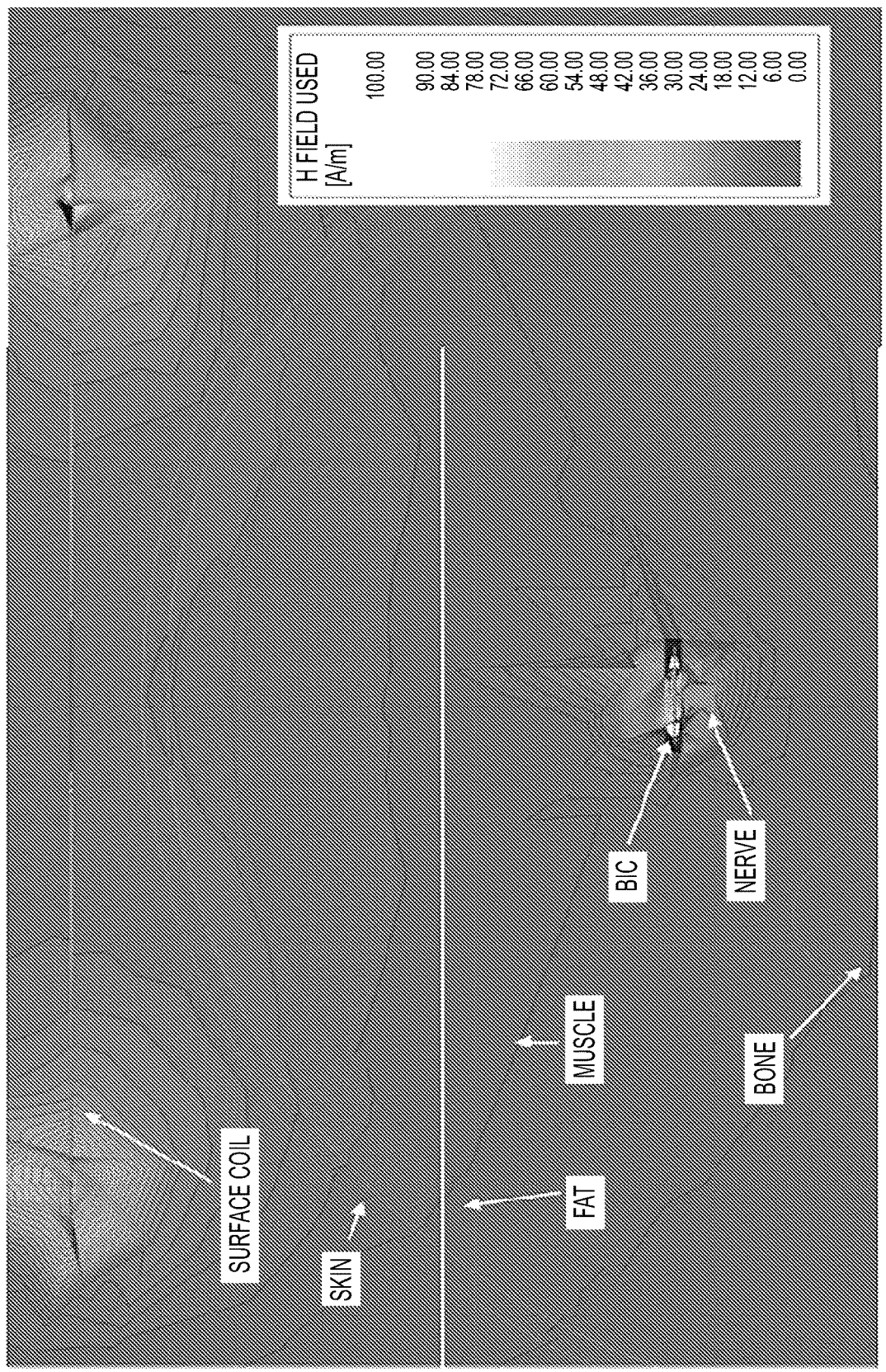
FIG. 3 is a drawing illustrating an exemplary simulated magnetic field map of a BIC implanted in the forearm adjacent to the median nerve and inductively coupled to a surface coil.

For this example scenario, Ansys HFSS software was used to simulate the magnetic field map generated at 127 MHz by a 6 mm diameter circular BIC coupled to a 38.75 mm diameter surface coil, which was driven with 1 W of power. The BIC was arranged coaxially with the surface coil, with 35.1 mm separation, and the nerve was an additional 1.5 mm below the BIC. FIG. 3 is a drawing illustrating an exemplary simulated magnetic field map of a BIC implanted in the forearm adjacent to the median nerve and inductively coupled to a surface coil. As apparent in FIG. 3, the BIC results in a concentrated magnetic field over a local region, which provides increased signal sensitivity, decreased noise from inductive losses in the sample, and a much smaller minimum FOV. FIG. 3 is essentially a numerical simulation showing the magnetic field intensity map, demonstrating how a coupled coil system functions.

Figure 4A:
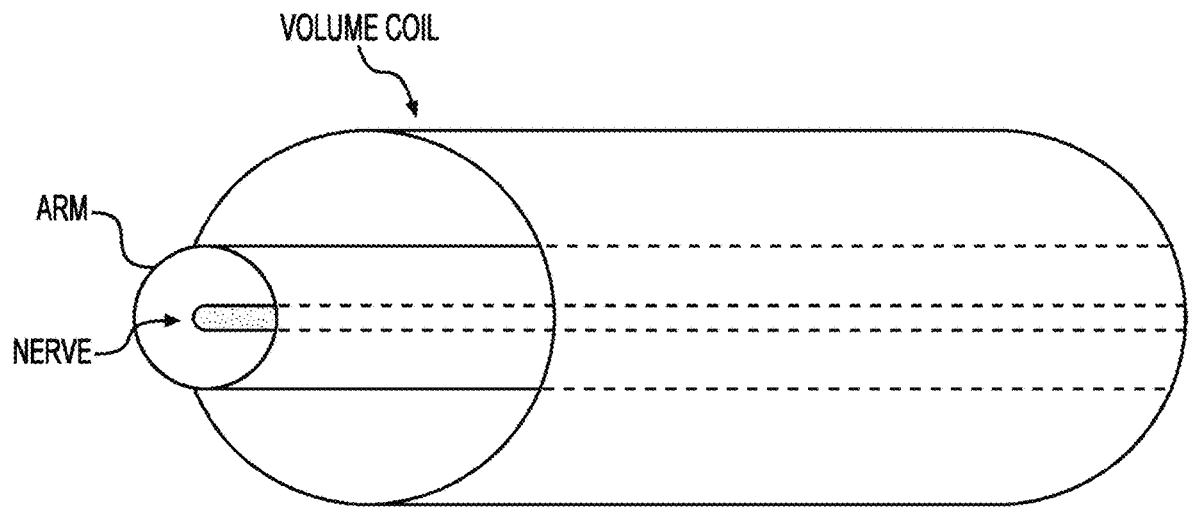
FIG. 4A is a drawing illustrating a 140 mm-diameter birdcage volume coil.
Figure 4B:
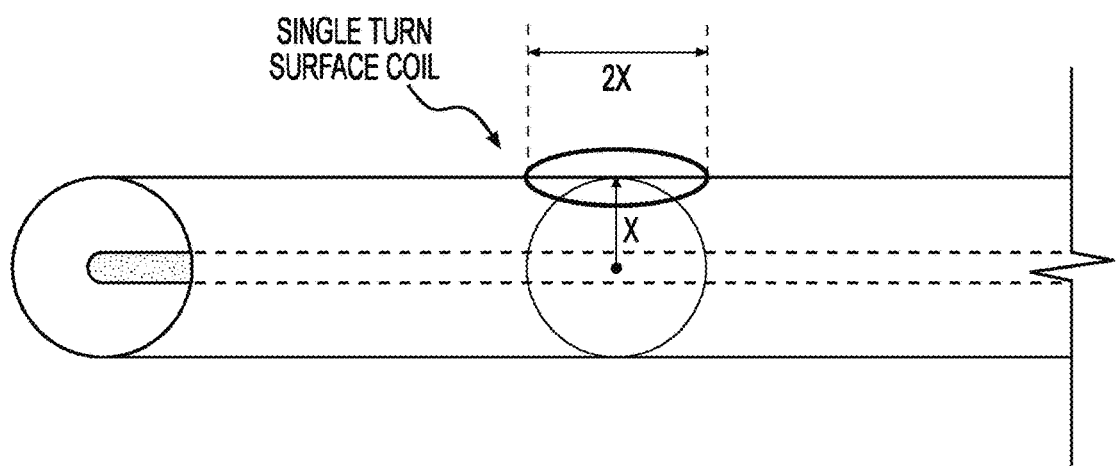
FIG. 4B is a drawing illustrating a single-turn surface coil with a diameter equal to 2× the depth of the nerve.
Figure 4C:
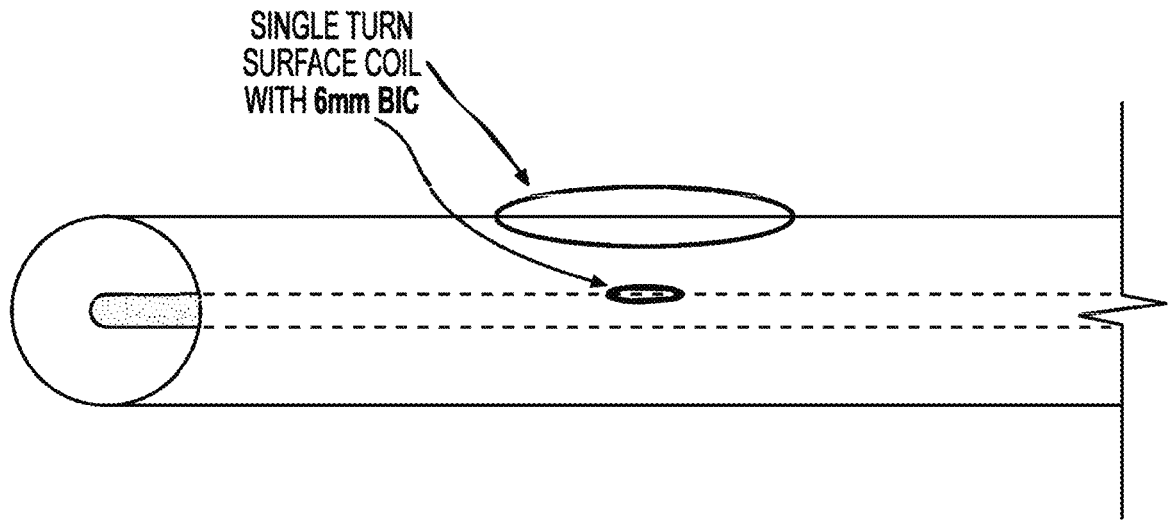
FIG. 4C is a drawing illustrating a 6 mm diameter BIC coupled to the single-turn surface coil shown in FIG. 4B.
Figure 4D:
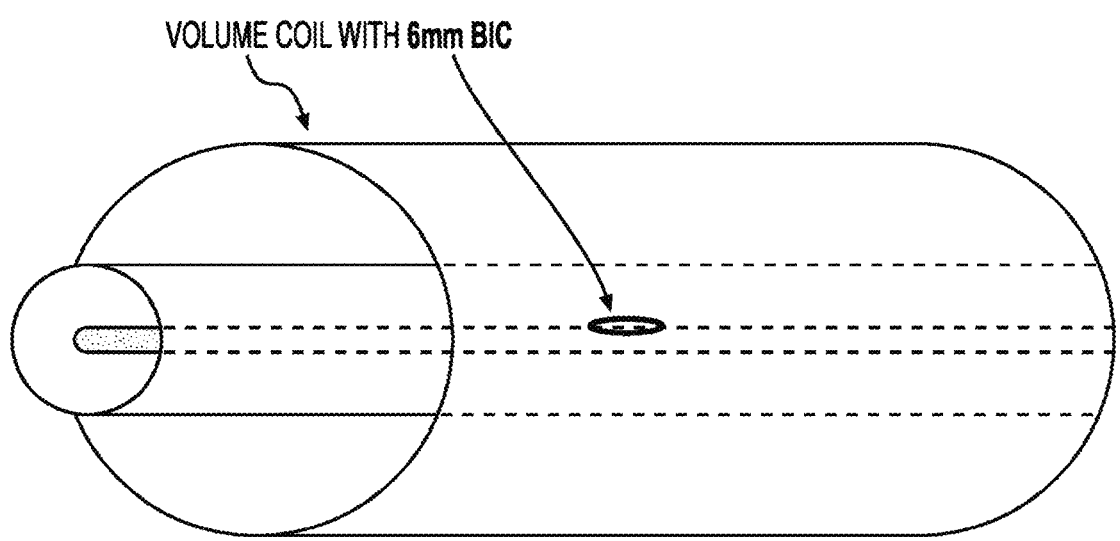
FIG. 4D is a drawing illustrating the BIC shown in FIG. 4C coupled to the birdcage volume coil shown in FIG. 4A.

This simulation did not incorporate measures of noise variance, and so a quantitative estimate of SNR gain from using this BIC was computed following the analytical approach of previous work. Four exemplary coil configurations were modeled in FIGS. 4A-4D. FIG. 4A is a drawing illustrating a 140 mm-diameter birdcage volume coil, FIG. 4B is a drawing illustrating a single-turn surface coil with a diameter equal to 2× the depth of the nerve, FIG. 4C is a drawing illustrating a 6 mm diameter BIC coupled to the single-turn surface coil shown in FIG. 4B, and FIG. 4D is a drawing illustrating the BIC shown in FIG. 4C coupled to the birdcage volume coil shown in FIG. 4A.

The SNR advantage of the BIC over a volume or surface receive coil will depend on the relative effective resistances (including tissue loading) of each coil. Higher resistance results in greater thermal noise. The volume and surface coils may be made from copper with material resistivity $\rho_{Cu} \approx 17$ n$\Omega$m, and this was used in the example calculations below. Alternatively, the BIC can be made from other bioresorbable conductors, such as molybdenum, zinc, magnesium, or tungsten, which have resistivities in the 40-55 n$\Omega$m range and higher ($\approx$100-1000 n$\Omega$m) in an oxidized state. For the example calculations, the inventors used molybdenum oxide ($MoO_2$) as the conductor for the BIC, with resistivity $\rho_{MoO2}=880$ n$\Omega$m. Alternatively, other conductors for the BIC may comprise unoxidized or oxidized molybdenum (Mo), magnesium (Mg), tungsten (W), zinc (Zn), carbon-based conductor, polymer, or combinations thereof. The effective resistances from inductive loses were modeled assuming a spherical sample filling 80% of the volume coil diameter for the configuration of FIG. 4A assuming an infinite half-space of tissue immediately adjacent the surface coil in the configuration of FIG. 4B, and an infinite space surrounding the BIC for the configurations of FIG. 4C and FIG. 4D. The root-mean-square (rms) electromotive force (emf) resulting from magnetization in the nerve was calculated for each of three detecting coils based on geometry. For this, the nerve was assumed to be offset from the BIC by 1.5 mm and from the surface coil by 1 coil radius. Likewise, geometry was used to calculate the mutual inductances between the BIC and both surface and volume coils, which were then used to transform the resistance and emf from the BIC to the appropriate pick-up coil for the configurations of FIG. 4C and FIG. 4D. The standard deviation of the noise ($\sigma$) was calculated for each case as proportional to the square-root of the total effective resistance at the pickup coil. Finally, the SNR at the pickup coil was computed as proportional to the ratio of emf and $\sigma$. These calculations were repeated for nerve depths 3 mm to 56 mm, and the resulting SNR values, normalized to those from the configuration of FIG. 4A, are plotted in FIG. 5. For this example calculation, which is for imaging the median nerve in the forearm, the volume coil is 140 mm in diameter.

Figure 2:
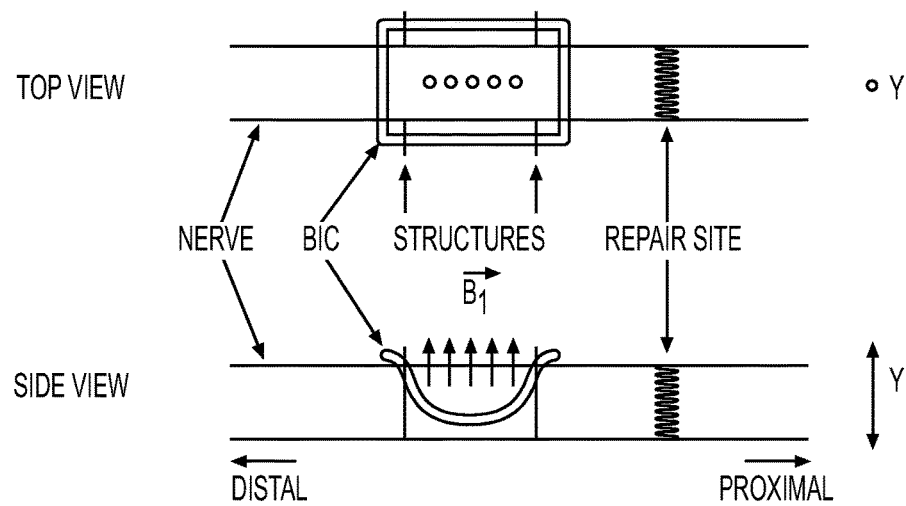
FIG. 2 is a drawing illustrating a saddle-shaped bioresorbable inductively-coupled coil (BIC) implanted on a nerve, 1-2 cm distal to a surgical repair site. Laboratory frame Y-direction (vertical in clinical magnet) is labeled on the right for each view.
Figure 5:
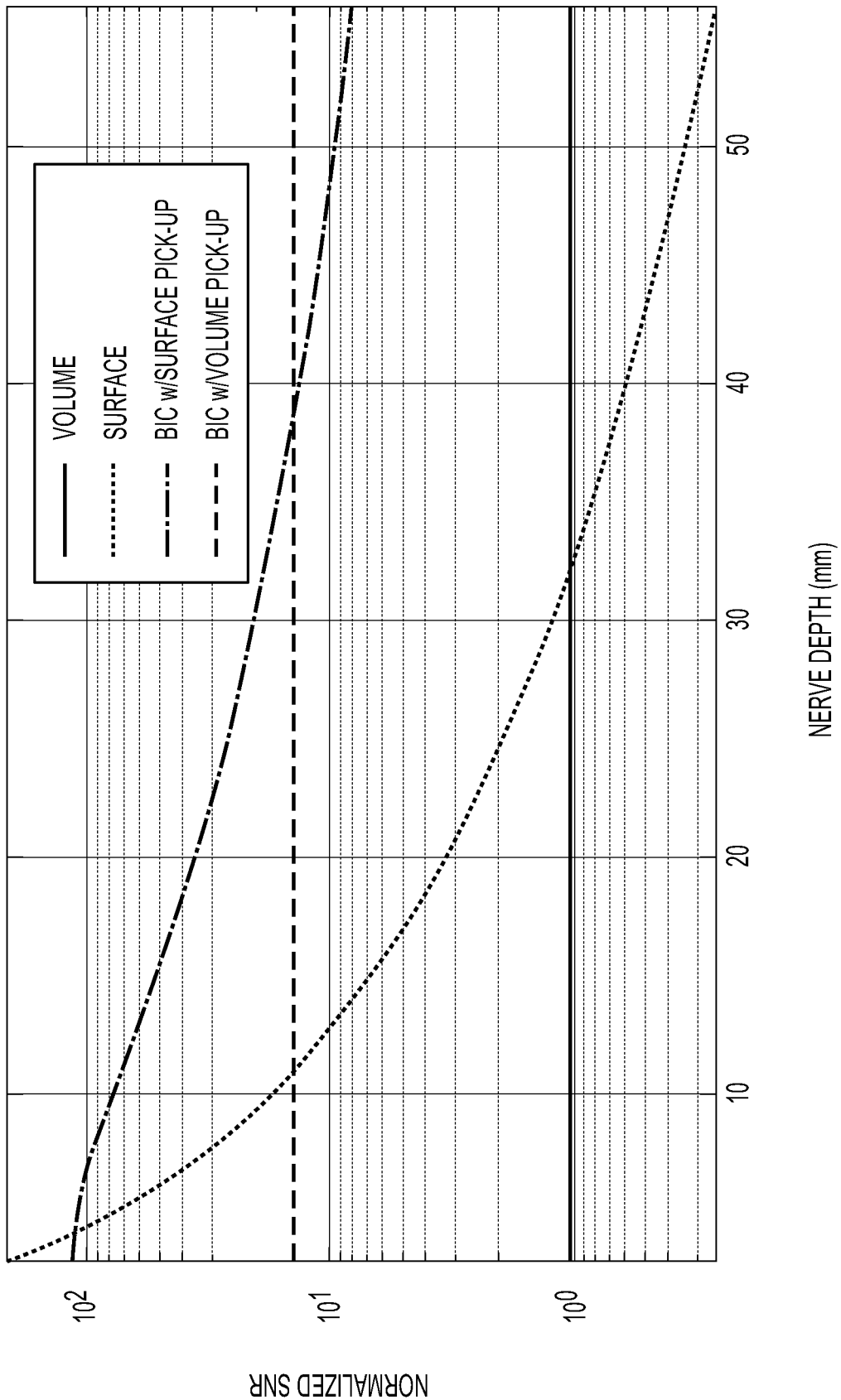
FIG. 5 is a plot illustrating calculated image SNR, for four different RF coil configurations (volume coil, surface coil, a BIC coupled to a surface coil, and a BIC coupled to a volume coil), normalized to that of a conventional volume coil.

FIG. 5 is a plot illustrating calculated image SNR, for four different RF coil configurations (volume coil, surface coil, a BIC coupled to a surface coil, and a BIC coupled to a volume coil), normalized to that of a conventional volume coil. FIG. 5 shows that for nerve depths mm, the BIC provides higher SNR than any other configuration. For nerve depths up to 39 mm, the surface coil is the best pick-up coil for the BIC, and for greater depths, the volume coil becomes a more efficient pick-up coil. Thus, for median nerve imaging in the forearm, the predicted SNR gain of the BIC is up to 14× compared with a near-optimally sized surface coil, and 14 to 100× compared with a birdcage volume coil. These SNR gains will only increase with more sophisticated BIC design (e.g., a saddle shape, as shown in FIG. 2, or even a birdcage that fully surrounds the nerve), and with deeper nerves in larger tissue cross-sections, such as in the upper arm or the thigh. FIG. 2 is a drawing illustrating a saddle-shaped bioresorbable inductively-coupled coil (BIC) implanted on a nerve, 1-2 cm distal to a surgical repair site. Laboratory frame Y-direction (vertical in clinical magnet) is labeled on the right for each view.

Figure 6:
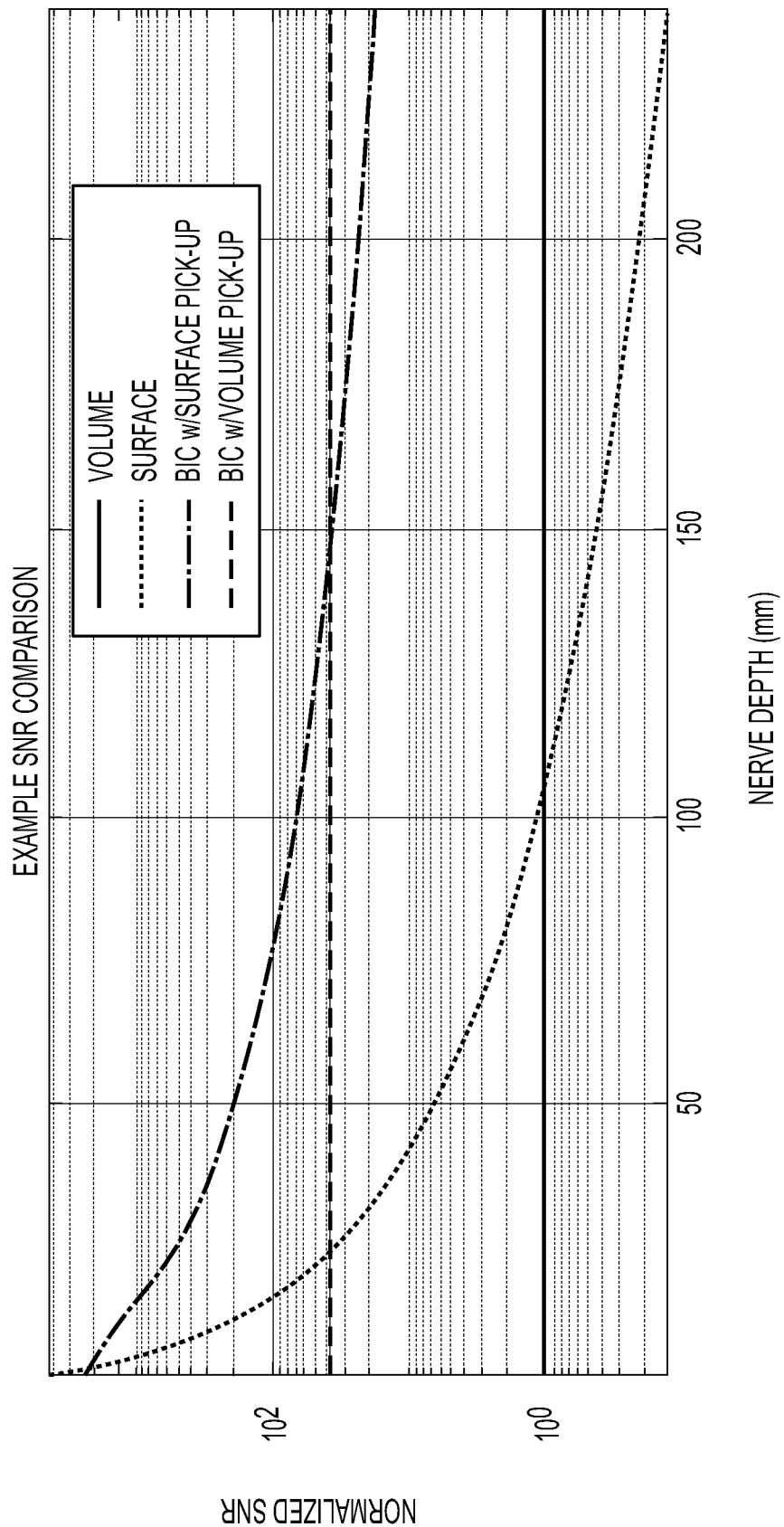
FIG. 6 is a plot similar to that shown in FIG. 5 but is representative of nerve imaging in the thigh, using a 30 cm diameter volume coil, with nerve depths up to 150 mm.

FIG. 6 is similar to FIG. 5 but is representative of nerve imaging in the thigh, and uses a 30 cm diameter volume coil, with nerve depths up to 150 mm. Here, for depths ≳4.4 mm the BIC provides higher SNR than any other configuration. For nerve depths up to ≈143 mm, the surface coil is the best pick-up coil for the BIC, and for greater depths, the volume coil becomes a more efficient pick-up coil. Thus, for nerve imaging in the thigh, the predicted SNR gain of the BIC is up to 40× compared with a near-optimally sized surface coil, and is 40 to 1000× compared with a birdcage volume coil.

There are many ways to wind a coil and what works best or even well enough will depend on the size, shape, and depth of the tissue of interest. With simplified model scenarios, relative SNR of BIC can be calculated vs. conventional surface or volume coils.

Specific Aims

A goal of this disclosure is to develop and evaluate implantable and bioresorbable radio frequency (RF) coils for high-resolution and high-specificity post-surgical monitoring with MRI. The immediate target application of this work is the evaluation or monitoring of peripheral nerve regeneration following surgical repair. However, other applications may be contemplated.

Surgical repair of a peripheral nerve is common following traumatic injury, but outcomes are highly variable and options for post-surgical evaluating or monitoring are limited. If regeneration is not occurring to a sufficient extent, an additional surgical procedure may be necessary. However, nerve regeneration is slow (~1 mm/day), and so it may take months before motor function is restored. During this time, muscles atrophy and the prospect for full functional recovery diminishes. If a surgeon must wait for clinical signs of reinnervation (or lack thereof) to determine if the initial procedure was successful (or not), then he/she may miss the window of opportunity for a surgical revision. Consequently, a clinical diagnostic that reports on the extent of nerve regeneration following surgical repair will enable earlier re-intervention and, in-turn, reduce the likelihood of long-term functional loss following a peripheral nerve injury.

MRI is an attractive option for evaluating nerve regeneration because it is minimally invasive and can provide quantitative measures related to tissue microstructure. However, nerves are relatively small (≤5 mm in diameter) and highly heterogenous (due to their fascicular structure and relatively large fraction of connective tissue). At the earliest post-surgical times, edema and the admixture of degenerating and regenerating processes contribute to even greater heterogeneity. Thus, it is a difficult to acquire MRI with sufficient spatial resolution and signal-to-noise ratio (SNR) for robust quantitative tissue characterization, particularly for post-surgical evaluating or monitoring.

The use of a small, local RF coil for MRI signal reception is known to substantially increase SNR and enable higher image resolution over a targeted volume of tissue. Surface coils are one example of this approach. But for deeper tissues, the greatest benefit results from surgically implanting a coil directly on/around the tissue of interest with wireless signal reception via inductive coupling. Such coils have been demonstrated effective in animal studies, but, for the most part, have not yet been applicable to clinical work. Recent advances in bioresorbable electronics are harnessed to create bioresorbable RF coils that are suitable for clinical applications. Specifically, this disclosure explores the design and function of bioresorbable implantable coils for the purpose of, for example, quantitatively evaluating or monitoring nerve regeneration following surgical repair. The work is presented in terms of the following two aims:

1. Design and Fabricate Bioresorbable RF Coils. Implantable RF coils will be designed in silico, produced as bioresorbable devices, and benchtop tested. In order to accommodate both pre-clinical and clinical studies, designs will be made for both 4.7 T (200 MHz) and 3.0 T (127 MHz) MRI systems. A variety of designs will be explored, including planar and cylindrical geometries, 1 to 20 mm in diameter, 1 to 10 cm operating depth, and both transmit/receive and receive-only. Coil designs will be evaluated based on: Q-factor, ability to tune and match remotely, volume & uniformity of coverage, and total metal mass.
2. Experimentally Evaluate Bioresorbable RF Coils. Implantable coils designed and fabricated in Aim 1 below will be evaluated through a series of experimental MRI studies. Coils will be implanted into gel phantoms for initial MRI evaluations of SNR, spatial coverage and uniformity, and sensitivity to pick-up coil geometry/positioning, and duration of function. Coils will then be surgically implanted into rats to evaluate in vivo MRI performance and functional longevity. As a preliminary evaluation of clinical translation, coils will be implanted into human cadaver arms for MRI evaluation on a clinical scanner. As a preliminary evaluation of clinical impact, coils will be used to evaluate nerve regeneration in an experimental sciatic nerve crush injury in rats.

Specific Aim 1: RF Coil Design and Fabrication

Each BIC may be designed using Ansys HFSS simulation software to meet functional characteristics outlined below, and then suitable designs will be fabricated using bioresorbable materials. The fabrication will start from patterning thin $MoO_2$ foils into wires using an ultraviolet laser cutter, followed by the transfer of the wires onto a biodegradable polymer sheet, polylactic-co-glycolic acid (PLGA), for better handling. Bioresorbable capacitors will be fabricated by sandwiching a PLGA film between two $MoO_2$ foil electrodes, and bioresorbable diodes (if necessary) by transferring a doped silicon nanomembrane p-n junction from a doped silicon-on-insulator (SOI) wafer onto PLGA. The coils will then be preferably coated in candelilla wax (or other well-tolerated material such as polyanhydrides as referenced in Choi, Y. S., Koo, J., Lee, Y. J., Lee, G., Avila, R., Ying, H., Reeder, J., Hambitzer, L., Im, K., Kim, J., Lee, K.-M., Cheng, J., Huang, Y., Kang, S.-K., Rogers, J. A., Biodegradable Polyanhydrides as Encapsulation Layers for Transient Electronics. *Adv. Funct. Mater.* 2020, 30, 2000941. https://doi.org/10.1002/adfm.202000941 to provide structural rigidity and a dielectric gap between the conductor and tissue. The wax serves as an insulating layer that insulates the coil from dielectric/signal losses by preventing dielectric coupling with surrounding tissue which would result in a drop-off of signal relative to the noise floor.

Design Variations

This disclosure aims to explore a variety of BIC-pick-up designs with different design variations.

Geometry: Essentially, the BIC is a loop conductor with one or more capacitors in series, or possibly in parallel, on a shunt circuit. The starting design will be a single-turn planar loop with a single series capacitor. Subsequent designs will include a half-saddle (see FIG. 2), full saddle, birdcage, or any shape that can provide a relatively uniform RF magnetic field ($\vec{B}_1$) over a cylindrical volume. Because most major nerves in the human body lie parallel to the coronal body plane, a BIC with this linearly-polarized design can be attached on/around most nerves while producing a $\vec{B}_1$ that is perpendicular to the static field (parallel to laboratory frame Y-direction, see FIG. 2) as needed for MRI. The pick-up will be a single-turn planar loop with variable capacitor for tuning. For deep nerves, it may be advantageous to use a conventional birdcage coil for the pick-up, as indicated in FIG. 5, in which case one of the existing coils will be used in linear mode. In order to accommodate a wide range of different nerves, BIC designs will be explored with receive fields 1 mm to 10 mm in cross-sectional diameter BIC-pick-up pairs separated by distances of 1 cm to 10 cm. Overall, the structure/configuration/shape/size of the coil would be dependent on the FOV and/or maximum sensitivity desired, and/or how easy the BIC is fixed in-place by a surgeon.

Coupling/Decoupling: Initial designs will use weakly-coupled BIC and pick-up systems, in which the BIC acts as both RF transmitter and receiver (Tx/Rx). This is the simplest approach but has some limitations. Weakly coupled systems, such as that used in the original WIMP can be tuned over a limited frequency range via a variable capacitor in the pick-up, with some cost in sensitivity. For greater tuning range and where enabled by coil geometry, over-coupled designs may be employed, which allow a greater tuning range that may be helpful for longitudinal studies in vivo (see, for example, Bilgen, M. (2006) Inductively-overcoupled coil design for high resolution magnetic resonance imaging BioMedical Engineering OnLine 5(1), 3. https://dx.doi.org/10.1186/1475-925x-5-3) A consequence of an over-coupled design is a stronger magnetic field in the tissue from the pick-up, which may reduce SNR and possible FOV reduction, and so quantitative experimental evaluations may assess the practical value of this approach. Finally, depending on the pace of progress, Rx-only designs may enable more uniform transmit $\vec{B}_1$ via a volume coil. This can be accomplished by passively detuning the BIC during transmission using, for example a cross-diode pair (and possibly a series inductor) in parallel with the main BIC loop—see, for example, FIG. 2a in Edelstein, W., Hardy, C., Resonance, O., 1986 (1986), Electronic decoupling of surface-coil receivers for NMR imaging and spectroscopy Elsevier 67(1), 156 161. https://dx-.doi.org/10.1016/0022-2364(86)90421-x.

Frequency: coils may resonate at, for example, 127 MHz, for a 3T clinical MRI system, and at 200 MHz coils for a 4.7 T pre-clinical MRI system.

Molybdenum Content: Two design considerations related to the conductor material are toxicity and resistivity, although neither are expected to be significant barriers to an effective BIC design. The dissolution rate of a $MoO_2$ in tissue is $1\times10^{-4}$ to $1\times10^{-3}$ μm/h; therefore, a 6 mm diameter $MoO_2$ BIC that is 1 mm wide×0.1 mm thick (as used in the example calculations, above), will dissolve at a maximum rate of ≈5.9 μg/d, about ⅔ of which is Mo. For comparison, the recommended daily allowance of dietary Mo is 45 μg. The resistivity of $MoO_2$ ($\rho_{MoO2}$) is ≈50×$\rho_{Cu}$, which will increase noise compared to a copper coil. However, as the example scenario above demonstrates, the increased noise from the BIC resistance is small compared to the decreased noise from the reduction of inductive losses. Coil resistance can, nonetheless, be further reduced by increasing the conductor cross-section, likely over the range of ≈100 μm to ≈1 mm, and so for each geometric design, the trade-off between total implanted mass of Mo and SNR gain provided by the BIC will be computed and experimentally tested. This will allow a BIC design that minimizes total implanted Mo while meeting a particular objective of SNR gain (e.g., 14× in the example scenario).

Functional Lifetime In Vivo: Nerve axons regenerate at 1 to 2 mm/d, so an ≈14 d delay can be expected before regenerating axons reach the center of a BIC FOV that is placed fully distal to the repair site. Electronics may be embedded in 300 μm-thick candelilla wax for this duration, and have shown that functional lifetime increases with increasing thickness. BICs may be fabricated by embedding in wax with thickness ranging 0.3 mm to 1.5 mm, and Aim 2 will test the duration of function of these BICs in gel phantoms and in rats.

Specific Aim 2: MRI Evaluations

The BICs developed in Aim 1 will be evaluated with MRI studies in phantoms, rats, and human cadaver arms. Observations from these studies will be fed back into the BIC design process in Aim 1. MRI studies of phantoms and rats will be performed at 200 MHz on a 4.7 T small animal scanner, and the human cadaver arm studies will be performed at 127 MHz on a clinical 3.0 T scanner. In all cases, SNR will be measured from samples/animals/tissue with and without a BIC, using standard spin-echo, diffusion-weighted spin-echo, and gradient-echo acquisitions. MRI studies will be repeated as noted below for each case.

Phantom Studies

To mimic a nerve, a cylinder (1 mm to 5 mm diameter) will be filled with 0.05 mM $MnCl_2$ in phosphate buffered saline (PBS) which is used to approximately replicate the conductivity of tissue. The BIC will be attached on/surrounding this cylinder and the combination will be implanted into a larger cylindrical phantom (10 mm to 100 mm diameter) containing tissue-mimicking agarose gel. Control phantoms will be made identically except without a BIC, MRI evaluations will provide experimental comparisons of SNR and spatial coverage in comparison to in silico and theoretical evaluations. Using BICs embedded in varying thicknesses of wax, MRI will be repeated weekly for up to 6 weeks to evaluate how degradation affects MRI performance.

Rat Studies

Rat studies will be used to evaluate the BIC in terms of ease of surgical implantation, SNR in vivo, functional lifetime, Mo accumulation in organs, and potential for characterizing regenerating nerve. Rats will be imaged before and after surgical implantation of a BIC on/surrounding the sciatic nerve, using slowly dissolving 4-0 Duracryl-PDS sutures. Every week following implantation, the MRI scans will be repeated and whole body μCT will be used to monitor the BIC degradation process. When the BIC fails or after 6 weeks, the rat will be euthanized and the BIC (or what remains of it) will be removed to evaluate its physical state and ascertain the cause of failure. Major organs (liver, kidney, spleen, quadriceps femoris muscle, and heart) will be harvested and Mo concentration in each will be measured by inductively coupled plasma optical emission spectroscopy. Finally, BIC designs that are demonstrated effective for more than 4 weeks will be tested in rats that have undergone experimental crush injury. In addition to providing preliminary data on the use of BICs for detecting nerve regeneration, histology of the regenerating nerves (6 weeks post-injury) will be compared to historical data as a preliminary test of the impact of BIC implantation on nerve regeneration.

Human Cadaver Studies

Lower arms (elbow to fingertip) from human cadavers will be acquired. MRI studies will be performed before and after surgically implantation of a BIC on/surrounding the median nerve at the mid-forearm level. Pre-implant, the scan protocol will match the current forearm nerve protocol (see Example Scenario, above). Post BIC implantation, the protocol will be revised to maximize in-plane spatial resolution, while matching the total scan times (≈20 min) and matching or exceeding the image SNR of the reference scans.

Rigor and Biological Variables

To ensure the results will be robust and unbiased, the following is noted: i) MRI and μCT instruments undergo routine Q/A testing, and ii) BIC designs will be evaluated at multiple levels—computer simulation, bench top, phantom. MRI, in vivo rat MRI, and in situ ex. vivo human MRI—and so overall conclusions of feasibility will be drawn from, results across all studies, not, any one in isolation. Only female rats will be used because they have a relatively stable weight in adulthood, making them well-suited for serial MRI studies; however, there is no reason to expect the BIC performance to depend on animal sex.

ADDITIONAL DESCRIPTION

Although embodiments are described above with reference to a BIC implanted for post-surgical peripheral nerve MRI, the BIC described in any of the above embodiments may alternatively be implanted for other post-surgical MRI uses. Such alternatives are considered to be within the spirit and scope of the present invention, and may therefore utilize the advantages of the configurations and embodiments described above.

In addition, although embodiments are described above with reference to a BIC implanted in a human, the BIC described in any of the above embodiments may alternatively be implanted in an animal. Such alternatives are considered to be within the spirit and scope of the present invention, and may therefore utilize the advantages of the configurations and embodiments described above.

The method steps in any of the embodiments described herein are not restricted to being performed in any particular order. Also, structures or systems mentioned in any of the method embodiments may utilize structures or systems mentioned in any of the device/system embodiments. Such structures or systems may be described in detail with respect to the device/system embodiments only but are applicable to any of the method embodiments.

Features in any of the embodiments described in this disclosure may be employed in combination with features in other embodiments described herein, such combinations are considered to be within the spirit and scope of the present invention.

The contemplated modifications and variations specifically mentioned in this disclosure are considered to be within the spirit and scope of the present invention.

More generally, even though the present disclosure and exemplary embodiments are described above with reference to the examples according to the accompanying drawings, it is to be understood that they are not restricted thereto. Rather, it is apparent to those skilled in the art that the disclosed embodiments can be modified in many ways without departing from the scope of the disclosure herein. Moreover, the terms and descriptions used herein are set forth by way of illustration only and are not meant as limitations. Those skilled in the art will recognize that many variations are possible within the spirit and scope of the disclosure as defined in the following claims, and their equivalents, in which all terms are to be understood in their broadest possible sense unless otherwise indicated.

The invention claimed is:

1. A bioresorbable radio frequency coil configured to be implanted in a patient, the bioresorbable radio frequency coil comprising a bioresorbable conductor configured to be resorbed within the patient while the bioresorbable radio frequency coil is implanted in the patient, wherein the bioresorbable radio frequency coil is shaped as a single-turn planar loop.

2. The bioresorbable radio frequency coil of claim 1, wherein the bioresorbable conductor is at least made of at least one of molybdenum, magnesium, tungsten, zinc, carbon-based conductor, or polymer.

3. The bioresorbable radio frequency coil of claim 2, wherein the at least one of the molybdenum, the magnesium, the tungsten, the zinc, the carbon-based conductor, or the polymer is oxidized.

4. A bioresorbable radio frequency coil configured to be implanted in a patient, the bioresorbable radio frequency coil comprising a bioresorbable conductor configured to be resorbed within the patient while the bioresorbable radio frequency coil is implanted in the patient, wherein the bioresorbable conductor is at least made of molybdenum oxide.

5. A bioresorbable radio frequency coil configured to be implanted in a patient, the bioresorbable radio frequency coil comprising a bioresorbable conductor configured to be resorbed within the patient while the bioresorbable radio frequency coil is implanted in the patient, wherein the bioresorbable radio frequency coil is shaped as a half-saddle.

6. The bioresorbable radio frequency coil of claim 1, wherein the bioresorbable radio frequency coil is an inductively-coupled coil.

7. An imaging system comprising:
a bioresorbable radio frequency coil configured to be implanted in a patient, the bioresorbable radio frequency coil comprising a bioresorbable conductor configured to be resorbed within the patient while the bioresorbable radio frequency coil is implanted in the patient; and
a magnetic resonance imaging device configured to image the patient using the bioresorbable radio frequency coil while the bioresorbable radio frequency coil is implanted in the patient.

8. The imaging system of claim 7, wherein the magnetic resonance imaging device is configured use the bioresorbable radio frequency coil to image peripheral nerve regeneration in the patient following surgical repair while the bioresorbable radio frequency coil is implanted in the patient.

9. The imaging system of claim 7, wherein the bioresorbable conductor is made of at least one of molybdenum, tungsten, zinc, carbon-based conductor, or polymer.

10. The imaging system of claim 9, wherein the at least one of the molybdenum, the tungsten, the zinc, the carbon-based conductor, or the polymer is oxidized.

11. The imaging system of claim 7, wherein the bioresorbable conductor is at least made of molybdenum oxide.

12. The imaging system of claim 7, wherein the bioresorbable radio frequency coil is an inductively-coupled coil.

13. A method for at least one of evaluating or monitoring a patient using a magnetic resonance imaging device, the method comprising:
implanting a bioresorbable radio frequency coil in the patient, the bioresorbable radio frequency coil comprising a bioresorbable conductor configured to be resorbed within the patient while the bioresorbable radio frequency coil is implanted in the patient; and
imaging the patient with the magnetic resonance imaging device using the bioresorbable radio frequency coil while the bioresorbable radio frequency coil is implanted in the patient.

14. The method of claim 13, wherein the imaging is performed post-surgery.

15. The method of claim 13, further comprising at least one of evaluating or monitoring peripheral nerve regeneration in the patient following surgical repair using the imaging.

16. The method of claim 13, wherein the bioresorbable conductor is at least made of molybdenum, tungsten, zinc, carbon-based conductor, or polymer.

17. The method of claim 16, wherein the at least one of the molybdenum, the tungsten, the zinc, the carbon-based conductor, or the polymer is oxidized.

18. The method of claim 13, wherein the bioresorbable conductor is at least made of molybdenum oxide.

19. The method of claim 13, wherein the imaging of the patient with the magnetic resonance imaging device using the bioresorbable radio frequency coil comprises inductively-coupling the bioresorbable radio frequency coil.

* * * * *